US012782294B2

(12) United States Patent
Cronin

(10) Patent No.: US 12,782,294 B2
(45) Date of Patent: Nov. 3, 2026

(54) METHOD TO ENHANCE A NON-INVASIVE RF ANALYTE DETECTION DEVICE

(71) Applicant: KNOW LABS, INC., Seattle, WA (US)

(72) Inventor: John Cronin, Seattle, WA (US)

(73) Assignee: KNOW LABS, INC., Seattle, WA (US)

( * ) Notice: Subject to any disclaimer, the term of this patent is extended or adjusted under 35 U.S.C. 154(b) by 250 days.

(21) Appl. No.: 18/606,259

(22) Filed: Mar. 15, 2024

(65) Prior Publication Data

US 2024/0310297 A1 Sep. 19, 2024

Related U.S. Application Data

(60) Provisional application No. 63/490,900, filed on Mar. 17, 2023.

(51) Int. Cl.
*G01N 22/00* (2006.01)
*G16C 20/64* (2019.01)
*G16H 50/70* (2018.01)

(52) U.S. Cl.
CPC ............ *G01N 22/00* (2013.01); *G16C 20/64* (2019.02); *G16H 50/70* (2018.01)

(58) Field of Classification Search
CPC ......... G01N 22/00; G16C 20/64; G16H 50/70
USPC ...................................................... 324/76.14
See application file for complete search history.

(56) References Cited

U.S. PATENT DOCUMENTS 4,202,000 A 5/1980 Carballes
6,762,867 B2 7/2004 Lippert et al.
8,223,021 B2 7/2012 Goodnow et al.
8,882,670 B2 11/2014 Hancock
9,198,607 B2 12/2015 Fischer
9,625,371 B2 4/2017 Furness, III et al.
(Continued)

FOREIGN PATENT DOCUMENTS

EP 3146898 B1 11/2018
EP 3981329 4/2022
(Continued)

OTHER PUBLICATIONS

International Search Report and Written Opinion issued for International Patent Application No. PCT/US2024/020287, Date of mailing: Jul. 16, 2024, 7 pages.

*Primary Examiner* — Roberto Velez
(74) *Attorney, Agent, or Firm* — HSML P.C.

(57) ABSTRACT

An enhanced noninvasive RF analyte detection device in which an enhancement database, an integration module, a transmission module, a sending enhancement module, and a receiving enhancement module are provided. The integration module determines the mode to detect a desired analyte, such as initiating the transmission module, sending enhancement module, and/or receiving enhancement module in a specific sequence. Once the mode is determined, the transmission module may send all of the transmit signals stored in the enhancement database, the sending enhancement module may transmit the signals related to the desired analyte that are stored in the enhancement module, and/or the receiving enhancement module may implement the receiving antenna settings for the desired analyte which are stored in the enhancement database.

19 Claims, 5 Drawing Sheets

(56) References Cited

U.S. PATENT DOCUMENTS

Figure 1:
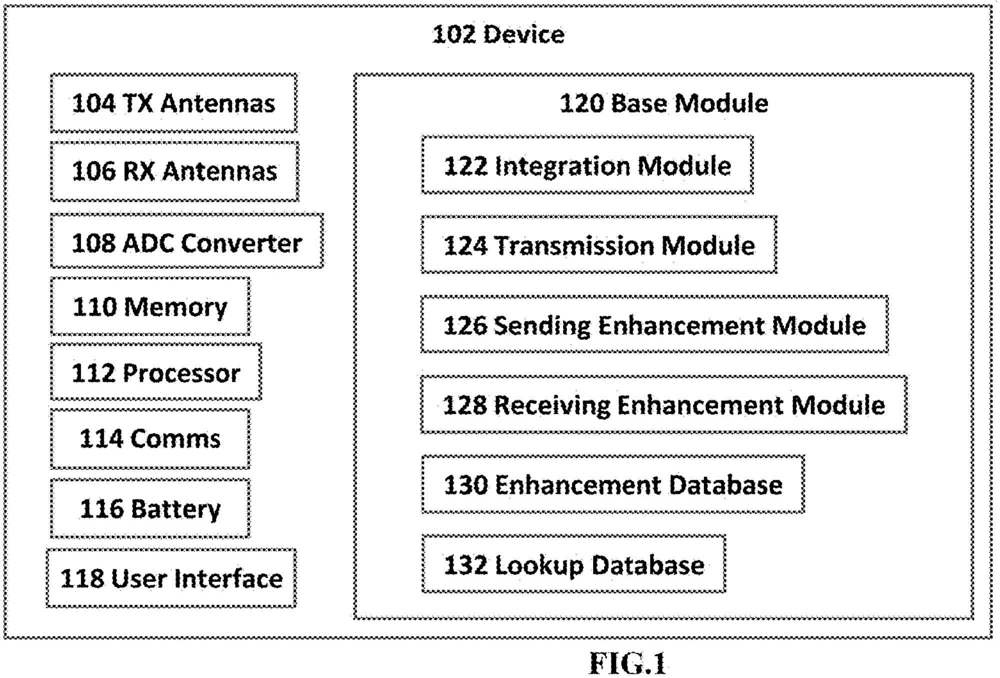

| | | | |
|---|---|---|---|
| 9,664,610 | B2 | 5/2017 | Mander et al. |
| 9,864,024 | B2 | 1/2018 | Vester |
| 10,149,629 | B2 | 12/2018 | Szczepaniak et al. |
| 10,258,268 | B2 | 4/2019 | Roblyer et al. |
| 10,478,101 | B1 | 11/2019 | Cespedes et al. |
| 10,548,503 | B2 | 2/2020 | Bosua |
| 10,617,296 | B2 | 4/2020 | Sloan et al. |
| 10,856,766 | B2 | 12/2020 | Leabman |
| 10,912,500 | B2 | 2/2021 | Poeze et al. |
| 10,956,950 | B2 | 3/2021 | Al-Ali et al. |
| 11,031,970 | B1 | 6/2021 | Bosua |
| 11,033,208 | B1 | 6/2021 | Bosua |
| 11,058,317 | B1 | 7/2021 | Bosua |
| 11,058,331 | B1 | 7/2021 | Bosua |
| 11,063,373 | B1 | 7/2021 | Bosua |
| 11,193,923 | B2 | 12/2021 | Bosua |
| 11,202,582 | B2 | 12/2021 | Verkruijsse et al. |
| 11,223,383 | B2 | 1/2022 | Bosua |
| 11,234,618 | B1 | 2/2022 | Bosua et al. |
| 11,234,619 | B2 | 2/2022 | Bosua |
| 11,244,753 | B2 | 2/2022 | Haggerty et al. |
| 11,284,819 | B1 | 3/2022 | Bosua et al. |
| 11,284,820 | B1 | 3/2022 | Bosua et al. |
| 11,291,374 | B2 | 4/2022 | Lee et al. |
| 11,298,037 | B2 | 4/2022 | Leabman |
| 11,330,997 | B2 | 5/2022 | Bosua |
| 11,350,830 | B2 | 6/2022 | Mckenna et al. |
| 11,360,188 | B2 | 6/2022 | Leabman |
| 11,367,525 | B2 | 6/2022 | Addison et al. |
| 11,389,091 | B2 | 7/2022 | Bosua |
| 11,389,093 | B2 | 7/2022 | Triman et al. |
| 11,426,104 | B2 | 8/2022 | Schurman et al. |
| 11,510,597 | B2 | 11/2022 | Bosua |
| 11,529,077 | B1 * | 12/2022 | Bosua .................... G16H 20/17 |
| 11,596,330 | B2 | 3/2023 | Hayter |
| 11,689,274 | B2 | 6/2023 | Bosua et al. |
| 11,696,698 | B1 | 7/2023 | Bosua |
| 11,764,488 | B2 | 9/2023 | Bosua et al. |
| 11,802,843 | B1 | 10/2023 | Bosua |
| 11,832,926 | B2 | 12/2023 | Bosua |
| 11,903,689 | B2 | 2/2024 | Bosua et al. |
| 11,903,701 | B1 | 2/2024 | Cronin |
| 2003/0036713 | A1 | 2/2003 | Bouton et al. |
| 2003/0235817 | A1 | 12/2003 | Bartkowiak et al. |
| 2004/0065158 | A1 | 4/2004 | Schrepfer et al. |
| 2004/0127777 | A1 | 7/2004 | Ruchti et al. |
| 2004/0133086 | A1 | 7/2004 | Ciurczak et al. |
| 2008/0083617 | A1 | 4/2008 | Simpson et al. |
| 2008/0214918 | A1 | 9/2008 | Brister et al. |
| 2008/0319285 | A1 | 12/2008 | Hancock |
| 2009/0099436 | A1 | 4/2009 | Brister et al. |
| 2009/0112101 | A1 | 4/2009 | Furness, III et al. |
| 2009/0137887 | A1 | 5/2009 | Shariati et al. |
| 2009/0275814 | A1 | 11/2009 | Watanabe et al. |
| 2010/0041969 | A1 | 2/2010 | Beise |
| 2011/0028814 | A1 | 2/2011 | Petersen et al. |
| 2013/0096396 | A1 | 4/2013 | Riedel |
| 2013/0184599 | A1 | 7/2013 | Friedman et al. |
| 2013/0289375 | A1 | 10/2013 | Fischer |
| 2014/0213870 | A1 | 7/2014 | Hsu et al. |
| 2015/0257698 | A1 | 9/2015 | Spratt et al. |
| 2016/0051171 | A1 | 2/2016 | Pikov et al. |
| 2016/0157733 | A1 | 6/2016 | Gil |
| 2016/0309535 | A1 | 10/2016 | Myoung et al. |
| 2016/0361002 | A1 | 12/2016 | Palikaras et al. |
| 2017/0095667 | A1 | 4/2017 | Yakovlev et al. |
| 2017/0164878 | A1 | 6/2017 | Connor |
| 2017/0215811 | A1 | 8/2017 | Newberry |
| 2017/0230084 | A1 | 8/2017 | Zhu et al. |
| 2017/0231568 | A1 * | 8/2017 | An ....................... A61B 5/0205 600/301 |
| 2018/0028824 | A1 | 2/2018 | Pivonka et al. |
| 2018/0035901 | A1 | 2/2018 | Cronin |
| 2018/0042559 | A1 | 2/2018 | Cabrera, Jr. |
| 2018/0132766 | A1 | 5/2018 | Lee et al. |
| 2018/0242920 | A1 | 8/2018 | Hresko et al. |
| 2018/0303391 | A1 | 10/2018 | Roblyer et al. |
| 2019/0008422 | A1 | 1/2019 | Leath et al. |
| 2019/0053741 | A1 | 2/2019 | Chaudhry |
| 2019/0104939 | A1 | 4/2019 | Costantine et al. |
| 2019/0117135 | A1 | 4/2019 | Wieder |
| 2019/0142313 | A1 | 5/2019 | Abou Ismail |
| 2019/0269853 | A1 | 9/2019 | Doyle et al. |
| 2019/0374135 | A1 | 12/2019 | Poeze et al. |
| 2019/0388000 | A1 | 12/2019 | Costantine et al. |
| 2020/0054255 | A1 | 2/2020 | Conrad et al. |
| 2020/0057163 | A1 | 2/2020 | Bromberg |
| 2020/0113485 | A1 | 4/2020 | Wybo et al. |
| 2020/0146584 | A1 | 5/2020 | Bosua |
| 2020/0178801 | A1 * | 6/2020 | Nazari ................. A61B 5/0031 |
| 2020/0187791 | A1 | 6/2020 | Leabman |
| 2020/0187792 | A1 | 6/2020 | Leabman |
| 2020/0187793 | A1 | 6/2020 | Leabman |
| 2020/0187812 | A1 | 6/2020 | Leabman |
| 2020/0187813 | A1 | 6/2020 | Leabman |
| 2020/0187814 | A1 | 6/2020 | Leabman |
| 2020/0187815 | A1 | 6/2020 | Leabman |
| 2020/0187816 | A1 | 6/2020 | Leabman |
| 2020/0187817 | A1 | 6/2020 | Leabman |
| 2020/0187818 | A1 | 6/2020 | Leabman |
| 2020/0187819 | A1 | 6/2020 | Leabman |
| 2020/0187820 | A1 | 6/2020 | Leabman |
| 2020/0187836 | A1 | 6/2020 | Leabman |
| 2020/0187837 | A1 | 6/2020 | Leabman |
| 2020/0187867 | A1 | 6/2020 | Leabman |
| 2020/0191909 | A1 | 6/2020 | Leabman |
| 2020/0191932 | A1 | 6/2020 | Leabman |
| 2020/0191933 | A1 | 6/2020 | Leabman |
| 2020/0191944 | A1 | 6/2020 | Leabman |
| 2020/0191945 | A1 | 6/2020 | Leabman |
| 2020/0191947 | A1 | 6/2020 | Leabman |
| 2020/0192426 | A1 | 6/2020 | Leabman |
| 2020/0192427 | A1 | 6/2020 | Leabman |
| 2020/0192428 | A1 | 6/2020 | Leabman |
| 2020/0193326 | A1 | 6/2020 | Leabman |
| 2020/0195197 | A1 | 6/2020 | Leabman |
| 2020/0195293 | A1 | 6/2020 | Leabman |
| 2021/0063366 | A1 | 3/2021 | Potyrailo et al. |
| 2021/0068715 | A1 | 3/2021 | Sloan et al. |
| 2021/0134431 | A1 | 5/2021 | Garcia et al. |
| 2021/0137468 | A1 | 5/2021 | Katragadda et al. |
| 2021/0142912 | A1 | 5/2021 | Belliveau et al. |
| 2021/0186357 | A1 | 6/2021 | Bosua et al. |
| 2021/0194531 | A1 | 6/2021 | Bosua |
| 2021/0205180 | A1 | 7/2021 | Pugsley |
| 2021/0219925 | A1 | 7/2021 | Au et al. |
| 2021/0244308 | A1 | 8/2021 | Bosua |
| 2021/0259571 | A1 | 8/2021 | Bosua |
| 2021/0259592 | A1 | 8/2021 | Bosua |
| 2021/0259593 | A1 | 8/2021 | Bosua |
| 2021/0307660 | A1 | 10/2021 | Chauhan et al. |
| 2021/0350896 | A1 | 11/2021 | Shelton, IV et al. |
| 2022/0015695 | A1 | 1/2022 | Margarito et al. |
| 2022/0031254 | A1 | 2/2022 | Al-Ali et al. |
| 2022/0071505 | A1 | 3/2022 | Bosua |
| 2022/0071523 | A1 | 3/2022 | Bosua |
| 2022/0071524 | A1 | 3/2022 | Bosua |
| 2022/0071527 | A1 | 3/2022 | Bosua |
| 2022/0074870 | A1 | 3/2022 | Bosua |
| 2022/0074871 | A1 | 3/2022 | Bosua |
| 2022/0077602 | A1 | 3/2022 | Bosua et al. |
| 2022/0077918 | A1 | 3/2022 | Bosua et al. |
| 2022/0151553 | A1 | 5/2022 | Bosua |
| 2022/0192494 | A1 | 6/2022 | Leabman |
| 2022/0192522 | A1 | 6/2022 | Leabman |
| 2022/0192531 | A1 * | 6/2022 | Leabman ............. A61B 5/7225 |
| 2022/0225899 | A1 | 7/2022 | Peterson et al. |
| 2022/0233119 | A1 | 7/2022 | Shelton, IV et al. |
| 2022/0233241 | A1 | 7/2022 | Shelton, IV |
| 2022/0238216 | A1 | 7/2022 | Shelton, IV et al. |
| 2022/0248965 | A1 | 8/2022 | O'Brien et al. |
| 2022/0248984 | A1 | 8/2022 | Poeze et al. |
| 2022/0257199 | A1 | 8/2022 | Breton et al. |
| 2022/0262477 | A1 | 8/2022 | Li et al. |

(56) References Cited

U.S. PATENT DOCUMENTS

| | | | |
|---|---|---|---|
| 2022/0287595 | A1 | 9/2022 | Bosua et al. |
| 2022/0287649 | A1 | 9/2022 | Leabman |
| 2022/0296111 | A1 | 9/2022 | Leabman |
| 2022/0322976 | A1 | 10/2022 | Edla |
| 2023/0233108 | A1 | 7/2023 | Bosua |
| 2023/0236166 | A1 | 7/2023 | Bosua |
| 2023/0263439 | A1 | 8/2023 | Cheng et al. |
| 2023/0390466 | A1 | 12/2023 | Johnson |
| 2024/0062870 | A1 | 2/2024 | Rosenberg et al. |

FOREIGN PATENT DOCUMENTS

| | | | |
|---|---|---|---|
| JP | 2012125382 | | 7/2012 |
| JP | 2014147637 | | 8/2014 |
| KR | 1020130110190 | A | 10/2013 |
| KR | 1020160081740 | | 7/2016 |
| KR | 1020200145694 | A | 12/2020 |
| KR | 1020210066332 | A | 6/2021 |
| WO | 2009/082286 | | 7/2009 |
| WO | 2016059635 | A1 | 4/2016 |
| WO | 2017163245 | | 9/2017 |
| WO | 2018/111690 | | 6/2018 |
| WO | 2019071138 | | 4/2019 |
| WO | 2019/178524 | | 9/2019 |
| WO | 2019182638 | | 9/2019 |
| WO | 2019217461 | | 11/2019 |
| WO | 2020006077 | | 1/2020 |
| WO | 2020037171 | | 2/2020 |
| WO | 2021124275 | A1 | 6/2021 |
| WO | 2021198045 | | 10/2021 |
| WO | 2021245459 | A1 | 12/2021 |
| WO | 2022026623 | | 2/2022 |
| WO | 2022/157706 | | 7/2022 |
| WO | 2022217304 | A1 | 10/2022 |
| WO | 2023/028367 | | 3/2023 |

* cited by examiner

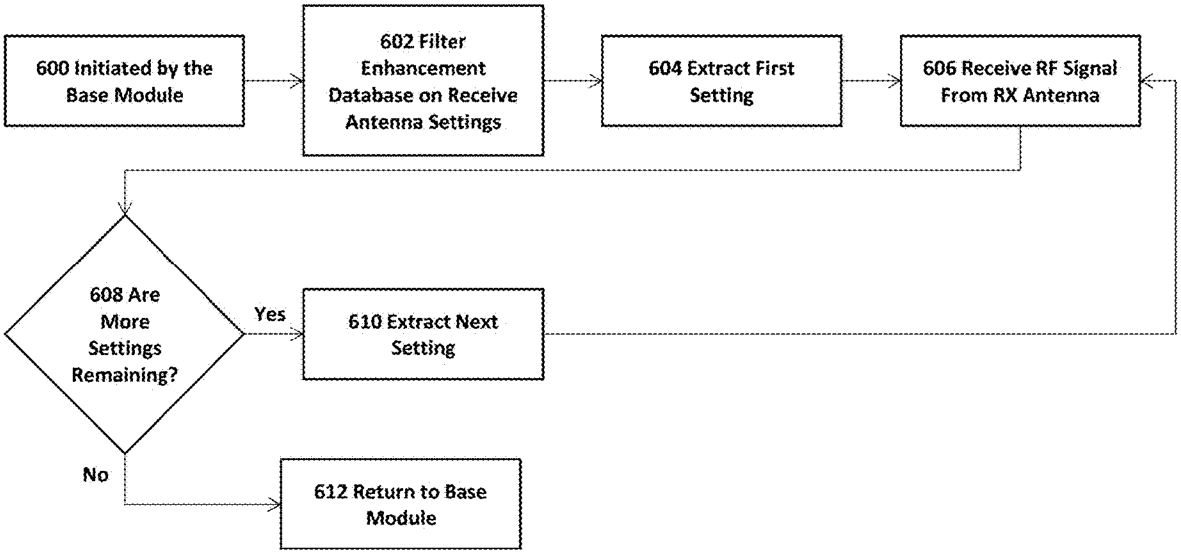

FIG.6

| Transmission Signal ID | RF Transmit Signal | Transmit Signal Length | RX Receive Signal | Filter Settings | Analyte |
|---|---|---|---|---|---|
| GLU-0001 | 120 Ghz | 10 ms | 100 GHz | Low Pass Filter | Glucose |
| GLU-0002 | 121 GHz | 10 ms | 101 GHZ | Low Pass Filter | Glucose |
| GLU-0003 | 122 GHz | 10 ms | 102 GHZ | Low Pass Filter | Glucose |
| - | - | | - | - | - |
| SOD-0001 | 500 MHz | 25 ms | 400 MHz | Band Pass Filter | Sodium |
| SOD-0002 | 510 MHz | 25 ms | 410 MHz | Band Pass Filter | Sodium |
| SOD-0003 | 520 MHz | 25 ms | 420 MHz | Band Pass Filter | Sodium |
| - | - | | - | - | - |
| POT-0001 | 900 MHz | 15 ms | 800 MHz | Low Pass Filter | Potassium |
| POT-0002 | 910 MHZ | 15 ms | 810 MHz | Low Pass Filter | Potassium |
| POT-0003 | 920 MHZ | 15 ms | 820 MHz | Low Pass Filter | Potassium |
| - | - | | - | - | - |
| - | - | | - | - | - |
| - | - | | - | - | - |

FIG.7

| Mode | Module 1 | Module 2 | Module 3 | Analyte |
|---|---|---|---|---|
| 1 | Sending Enhancement Module | Receiving Enhancement Module | N/A | Glucose |
| 2 | Transmission Module | N/A | N/A | Sodium |
| 3 | Transmission Module | Receiving Enhancement Module | N/A | Potassium |
| 4 | Transmission Module | Sending Enhancement Module | Receiving Enhancement Module | Chloride |
| - | - | - | - | - |
| - | - | - | - | - |
| - | - | - | - | - |

FIG.8

METHOD TO ENHANCE A NON-INVASIVE RF ANALYTE DETECTION DEVICE

FIELD

The present disclosure is generally related to enhancing a noninvasive RF analyte detection device.

BACKGROUND

Currently, detecting a specific analyte using a radio frequency signal is difficult since there are numerous transmit signals that could be sent as well as numerous settings that may be implemented to receive a specific signal. Also, it is time consuming to determine which transmitted signals, filter settings, receive signals, etc. are related to a specific analyte. Lastly, there is a challenge to prevent noise issues when sending and receiving the signals, such as transmitting the wrong signals, sending the correct signals for the wrong duration, incorrectly tuned amplifiers, receiving unwanted signals, etc. Thus, there is a need in the prior art to provide an enhanced noninvasive RF analyte detection device.

SUMMARY

An enhanced noninvasive RF analyte detection device in which an enhancement database, an integration module, a transmission module, a sending enhancement module, and a receiving enhancement module are provided. The integration module determines the mode to detect a desired analyte, such as initiating the transmission module, sending enhancement module, and/or receiving enhancement module in a specific sequence. Once the mode is determined, the transmission module may send all of the transmit signals stored in the enhancement database, the sending enhancement module may transmit the signals related to the desired analyte that are stored in the enhancement module, and/or the receiving enhancement module may implement the receiving antenna settings for the desired analyte which are stored in the enhancement database.

A method to enhance a noninvasive RF analyte detection device can include providing a noninvasive RF analyte detection; providing an enhancement database; providing a transmission module; providing a sending enhancement module; providing a receiving enhancement module; and providing an integration module. The method includes executing the sending enhancement module and the receiving enhancement module to send and receive signals to the transmission module respectively, and execute the integration module before or after sending and receiving signals to the transmission module respectively.

A non-invasive analyte detection system can include a non-invasive radio-frequency (RF) analyte detection device that includes one or more transmit antennas configured to transmit RF analyte detection signals from the one or more transmit antennas into a user, and one or more receive antennas that receive return RF analyte signals that result from the RF analyte detection signals transmitted into the user; the non-invasive RF analyte detection device is configured to perform an analyte detection routine using the one or more transmit antennas and the one or more receive antennas. The system can further include an analog-to-digital converter connected to the one or more receive antennas; a look-up database that includes a plurality of stored modes with each stored mode including at least one executable module to be executed and a corresponding analyte, and the stored modes are different from one another; and an enhancement database that includes a plurality of stored transmission signal procedures with each stored transmission signal procedure including an RF transmit signal to be transmitted, an expected RF received signal corresponding to the RF transmit signal, and an associated analyte, and the stored transmission signal procedures are different from one another.

Another example of a non-invasive analyte detection system can include a non-invasive radio-frequency (RF) analyte detection device that includes one or more transmit antennas configured to transmit RF analyte detection signals from the one or more transmit antennas into a user, and one or more receive antennas that receive return RF analyte signals that result from the RF analyte detection signals transmitted into the user; the non-invasive RF analyte detection device is configured to perform an analyte detection routine using the one or more transmit antennas and the one or more receive antennas. The system can further include an analog-to-digital converter connected to the one or more receive antennas; a user interface that is configured to allow user input of an analyte to be detected during the analyte detection routine; a look-up database that includes a plurality of stored modes each of which includes at least one executable module to be executed and a corresponding analyte, and the stored modes are different from one another; and an enhancement database that includes a plurality of stored transmission signal procedures each of which includes an RF transmit signal to be transmitted, an expected RF received signal corresponding to the RF transmit signal, and an associated analyte, and the stored transmission signal procedures are different from one another.

A non-invasive analyte detection method can include providing a non-invasive radio-frequency (RF) analyte detection device that includes one or more transmit antennas configured to transmit RF analyte detection signals from the one or more transmit antennas into a user, and one or more receive antennas that receive return RF analyte signals that result from the RF analyte detection signals transmitted into the user; the non-invasive RF analyte detection device is configured to perform an analyte detection routine using the one or more transmit antennas and the one or more receive antennas. The method can further include receiving a selection of a desired analyte to be detected by the non-invasive RF analyte detection device, and based on the desired analyte, accessing a look-up database and comparing the desired analyte to a plurality of stored modes each of which includes at least one corresponding executable module to be executed and a corresponding analyte. If one of the stored modes has a corresponding analyte that corresponds to the desired analyte, the one stored mode is selected and the at least one corresponding executable module of the one stored mode is extracted. Thereafter, the extracted at least one corresponding executable module accesses an enhancement database that includes a plurality of stored transmission signal procedures each of which includes an RF transmit signal to be transmitted, an expected RF received signal corresponding to the RF transmit signal, and an associated analyte. Thereafter, the extracted at least one corresponding executable module executes one or more of the stored transmission signal procedures having an associated analyte that corresponds to the desired analyte.

DRAWINGS

FIG. 1: Illustrates a noninvasive RF analyte detection device, according to an embodiment.

Figure 2:
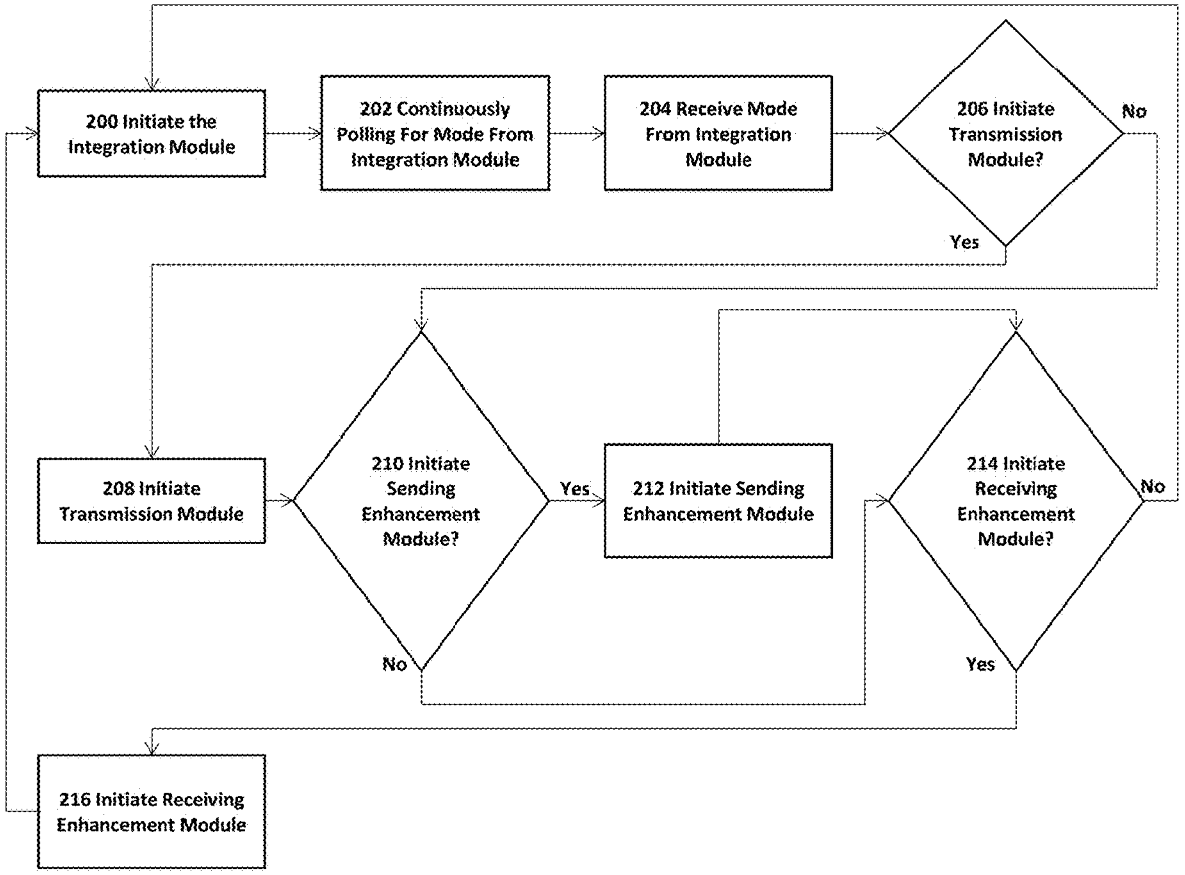

FIG. 2: Illustrates an example operation of a Base Module, according to an embodiment.

Figure 3:
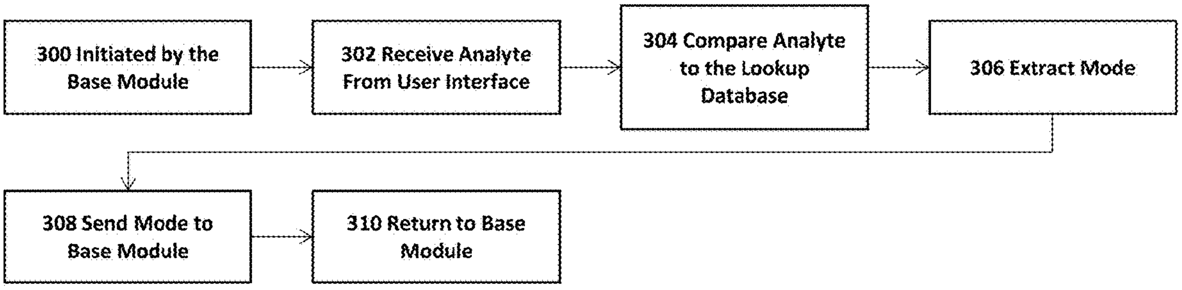

FIG. 3: Illustrates an example operation of an Integration Module, according to an embodiment.

Figure 4:
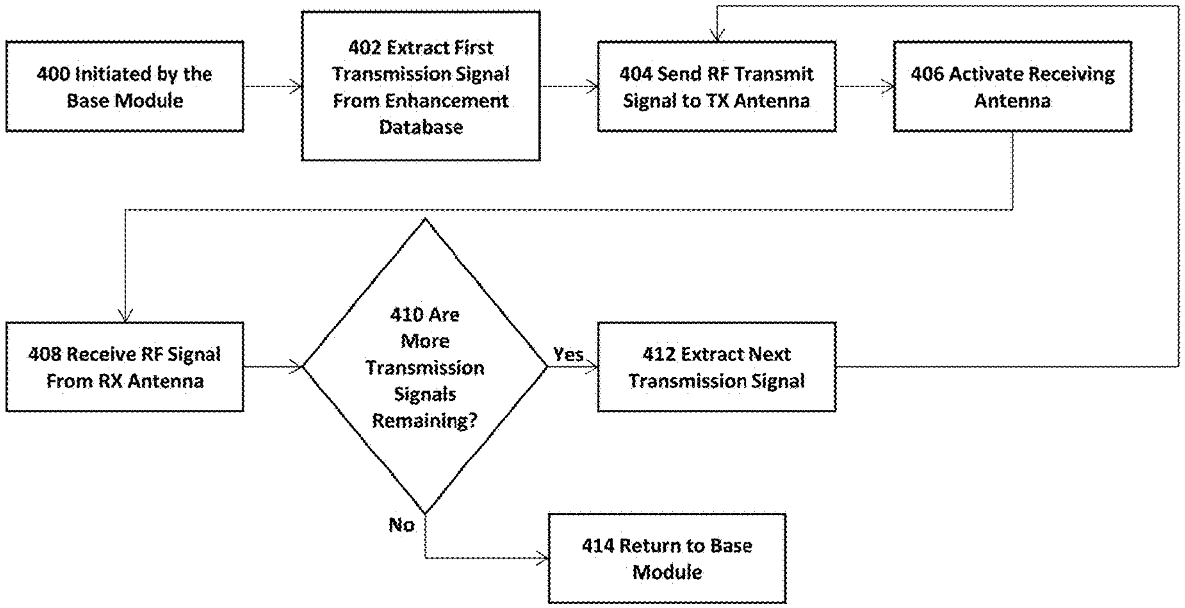

FIG. 4: Illustrates an example operation of a Transmission Module, according to an embodiment.

Figure 5:
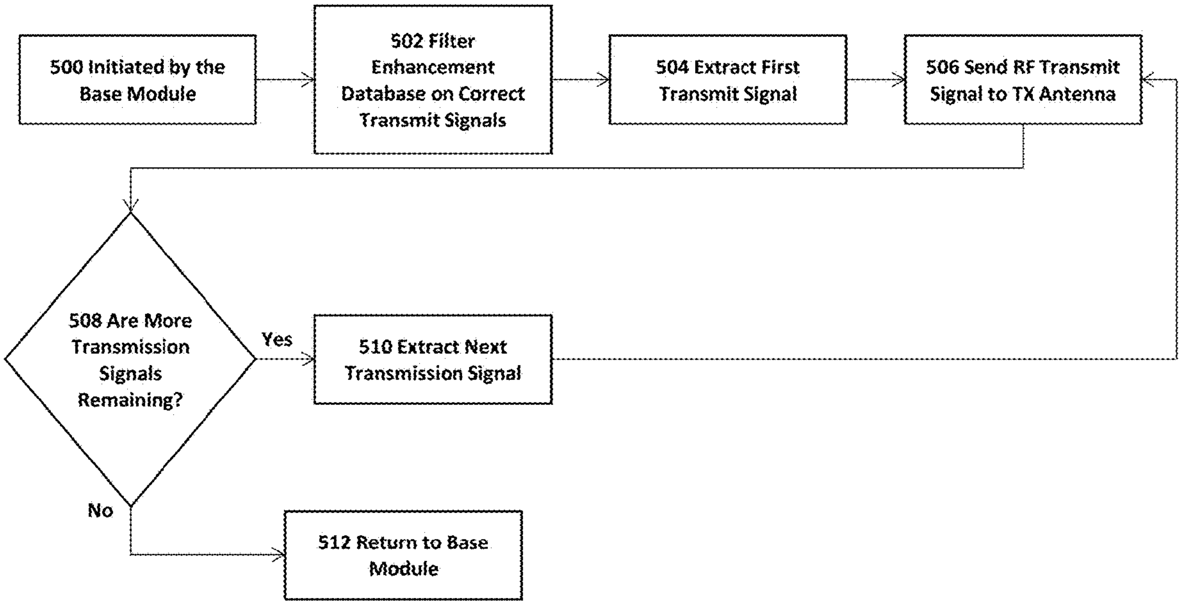

FIG. 5: Illustrates an example operation of a Sending Enhancement Module, according to an embodiment.

FIG. 6: Illustrates an example operation of a Receiving Enhancement Module, according to an embodiment.

FIG. 7: Illustrates an Enhancement Database, according to an embodiment.

FIG. 8: Illustrates a Lookup Database, according to an embodiment.

DETAILED DESCRIPTION

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

U.S. Pat. Nos. 10,548,503, 11,063,373, 11,058,331, 11,033,208, 11,284,819, 11,284,820, 10,548,503, 11,234,619, 11,031,970, 11,223,383, 11,058,317, 11,193,923, 11,234,618, 11,389,091, U.S. 2021/0259571, U.S. 2022/0077918, U.S. 2022/0071527, U.S. 2022/0074870, U.S. 2022/0151553, are each individually incorporated herein by reference in their entirety.

FIG. 1 illustrates a system providing a noninvasive RF analyte detection device. This system comprises a device 102, such as a noninvasive RF analyte detection device, that adjusts the transmitted signals to receive the necessary signals to properly detect a desired analyte. The device 102 may contain a plurality of TX antennas 104, a plurality of RX antennas 106, an ADC converter 108, memory 110, processor 112, communication module 114, battery 116, user interface 118, and a base module 120 which initiates an integration module 122, a transmission module 124, a sending enhancement module 126, a receiving enhancement module 128, and utilizes data stored in an enhancement database 130 and lookup database 132.

Further, embodiments may include a plurality of TX antennas 104 which may be integrated into the circuitry arrangement. The one or more TX antennas 104 may be configured to transmit the activated RF range signals at a pre-defined frequency. In one embodiment, the pre-defined frequency may correspond to a range suitable for the human body. For example, the one or more TX antennas 104 transmit Activated RF range signals at a range of 122-126 GHz.

Further, embodiments may include a plurality of RX antennas 106 which may be integrated into the circuitry arrangement. The one or more RX antennas 106 may be configured to receive the responded portion of the activated RF range signals. In one embodiment, the Activated RF range signals may be transmitted into the user, and electromagnetic energy may be responded from many parts such as fibrous tissue, muscle, tendons, bones, and the skin. It can be noted that effective monitoring of the blood glucose level is facilitated by an electrical response of blood molecules, such as pancreatic endocrine hormones, against the transmitted activated RF range signals. It will be apparent to a skilled person that the pancreatic endocrine hormones such as insulin and glucagon are responsible for maintaining sugar or glucose level. Further, the electromagnetic energy responded from the blood molecules may be received by the one or more RX antennas 106.

Further, embodiments may include an ADC Converter 108 which may be coupled to the one or more RX antennas 106. The one or more RX antennas 106 may be configured to receive the responded activated RF range signals. The ADC 108 may be configured to convert the responded activated RF range signals from an analog signal into a digital processor readable format signal.

Further, embodiments may include a memory 110 that may be configured to store the transmitted activated RF range signals by the one or more TX antennas 104 and receive a responded portion of the transmitted activated RF range signals from the one or more RX antennas 106. Further, the memory 110 may also store the converted digital processor readable format by the ADC 108. In one embodiment, the memory 110 may include suitable logic, circuitry, and/or interfaces that may be configured to store a machine code and/or a computer program with at least one code section executable by the processor 112. Examples of implementation of the memory 110 may include, but are not limited to, Random Access Memory (RAM), Read Only Memory (ROM), Hard Disk Drive (HDD), and/or a Secure Digital (SD) card.

Further, embodiments may include a processor 112 which may facilitate the operation of the device 102 to perform functions according to the instructions stored in the memory 110. In one embodiment, the processor 112 may include suitable logic, circuitry, interfaces, and/or code that may be configured to execute a set of instructions stored in the memory 110. The processor 112 may be configured to run the instructions obtained by the device base module 120 to perform polling. The processor 112 may be further configured to collect real-time signals from the one or more TX antennas 104 and the one or more RX antennas 106 and may store the real-time signals in the memory 110. In one embodiment, the real-time signals may be assigned as initial and updated radio frequency (RF) signals. Examples of the processor 112 may be an X86-based processor, a Reduced Instruction Set Computing (RISC) processor, an Application-Specific Integrated Circuit (ASIC) processor, a Complex Instruction Set Computing (CISC) processor, and/or other processors. The processor 112 may be a multicore microcontroller specifically designed to carry multiple operations based upon pre-defined algorithm patterns to achieve the desired result. Further, the processor 112 may take inputs from the device 102 and retain control by sending signals to different parts of the device 102. The processor 112 may access a Random Access Memory (RAM) that is used to store data and other results created when the processor 112 is at work. It can be noted that the data is stored temporarily for further processing, such as filtering, correlation, correction, and adjustment. Moreover, the processor 112 carries out special tasks as programs that are pre-stored in the Read Only Memory (ROM). It can be noted that the special tasks carried out by the processor 112 indicate and apply certain actions which trigger specific responses.

Further, the communication module 114 of the device 102 may communicate with a device network via a cloud network. Examples of the communication module 114 may include, but are not limited to, the Internet, a cloud network, a Wireless Fidelity (Wi-Fi) network, a Wireless Local Area Network (WLAN), a Local Area Network (LAN), a telephone line (POTS), Long Term Evolution (LTE), and/or a Metropolitan Area Network (MAN). In one embodiment, various devices may be configured to have a communication module 114 integrated over circuitry arrangement to connect with a device network via various wired and wireless communication protocols, such as the cloud network. Examples of such wired and wireless communication protocols may include, but are not limited to, Transmission Control Protocol and Internet Protocol (TCP/IP), User Datagram Protocol (UDP), Hypertext Transfer Protocol (HTTP), File Transfer Protocol (FTP), Zigbee, EDGE, infrared (IR), IEEE® 802.11, 802.16, cellular communication protocols, and/or Bluetooth® (BT) communication protocols.

Further, embodiments may include a battery 116 to power hardware modules of the device 102. The device 102 may be configured with a charging port to recharge the battery 116. It can be noted that the charging of the battery 116 may be achieved via wired or wireless means. In one embodiment, the battery 116 may include different models of a lithium-ion battery, such as CR1216, CR2016, CR2032, CR2025, CR2430, CR1220, CR1620, CR1616.

Further, embodiments may include a user interface 118 which may either accept inputs from users or provide outputs to the users or may perform both the actions. For example, the user may input the desired analyte to be detected by the device 102. In one case, a user can interact with the interface(s) 118 using one or more user-interactive objects and devices. The user-interactive objects and devices may comprise user input buttons, switches, knobs, levers, keys, trackballs, touchpads, cameras, microphones, motion sensors, heat sensors, inertial sensors, touch sensors, or a combination of the above. Further, the interface(s) may either be implemented as a Command Line Interface (CLI), a Graphical User Interface (GUI), a voice interface, or a web-based user-interface.

Further, embodiments may include a base module 120 which begins by initiating the integration module 122. The base module 120 is continuously polling for the mode from the integration module 122. The base module 120 receives the mode from the integration module 122. In addition, the base module 120 determines if the transmission module 124 should be initiated. If it is determined that the transmission module 124 should be initiated, the base module 120 initiates the transmission module 124. If it is determined that the transmission module 124 should not be initiated or after the transmission module 124 is initiated, the base module 120 determines if the sending enhancement module 126 should be initiated. If it is determined that the transmission module 124 should be initiated, the base module 120 initiates the transmission module 124. If it is determined that the sending enhancement module 126 should not be initiated or after the sending enhancement module 126 is initiated, the base module 120 determines if the receiving enhancement module 128 should be initiated. If it is determined that the receiving enhancement module 128 should not be initiated, the base module 120 returns to initiating the integration module 122. If it is determined that the receiving enhancement module 128 should be initiated, the base module 120 initiates the receiving enhancement module 128.

Further, embodiments may include an integration module 122 which begins by being initiated by the base module 120. The integration module 122 receives the analyte from the user interface 118. The integration module 122 compares the received analyte from the user interface 118 to the lookup database 132. The integration module 122 extracts the mode from the lookup database 132. The integration module 122 sends the extracted mode to the base module 120. The integration module 122 then returns to the base module 120.

Further, embodiments may include a transmission module 124 which begins by being initiated by the base module 120. The transmission module 124 extracts the first transmission signal from the enhancement database 130. The transmission module 124 sends the RF transmit signal to the TX antenna 104. For example, the one or more TX antennas 104 may be configured to transmit the activated RF range signals at a pre-defined frequency. In one embodiment, the predefined frequency may correspond to a range suitable for the human body. For example, the one or more TX antennas 104 transmit activated RF range signals at a range of 122-126 GHz. The transmission module 124 also activates the RX antennas 106. The transmission module 124 receives the RF signal from the RX antenna 106. The transmission module 124 determines if more transmission signals are remaining in the enhancement database 130. If it is determined that more transmission signals remain in the enhancement database 130, the transmission module 124 extracts the next transmission signal from the enhancement database 130 and returns to sending the RF transmit signal to the TX antenna 104. If it is determined that no more transmission signals remain in the enhancement database 130, the transmission module 124 returns to the base module 120.

Further, embodiments may include a sending enhancement module 126 which begins with the sending enhancement module 126 being initiated by the base module 120. The sending enhancement module 126 filters the enhancement database 130 on the correct transmission signals. The sending enhancement module 126 extracts the first correct transmit signal from the enhancement database 130. The sending enhancement module 126 sends the correct transmit signal to the TX antenna 104. The sending enhancement module 126 determines if there are more transmit signals remaining in the enhancement database 130. If it is determined that there are more transmit signals remaining in the enhancement database 130, the sending enhancement module 126 extracts the next transmit signal from the enhancement database 130 and returns to sending the transmit signal to the TX antenna 104. If it is determined that there are no more transmit signals remaining in the enhancement database 130, the sending enhancement module 126 returns to the base module 120.

Further, embodiments may include a receiving enhancement module 128, which begins by being initiated by the base module 120. The receiving enhancement module 128 filters the enhancement database 130 on the correct receive antenna 106 settings. The receiving enhancement module 128 extracts the first setting from the enhancement database 130. The receiving enhancement module 128 receives the RF signal from the RX antenna 106 with the extracted settings from the enhancement database 130. The receiving enhancement module 128 determines if there are more settings remaining in the enhancement database 130. If it is determined that there are more settings remaining in the enhancement database 130, the receiving enhancement module 128 extracts the next setting in the enhancement database 130 and returns to receiving the RF signal from the RX antenna 106. If it is determined that there are no more settings remaining in the enhancement database 130, the receiving enhancement module 128 returns to the base module 120.

Further, embodiments may include an enhancement database 130 which may contain a plurality of transmission signal procedures which may include the transmission signal ID, the RF transmit signal, the duration the signal is transmitted, the expected received signal, the filter settings, and the analyte that may be detected during the procedure. The database 130 may be created using historical information collected in a clinical setting in which the transmit and received signals, as well as the duration and filter settings, are monitored to determine if an analyte is detected. The detection of the analyte may be based upon comparing the transmit signals and received signals to ground truth data collected by medical devices. For example, the database 130 may utilize a module that may be configured to execute a correlation between the real-time ground truth data and the RX converted data. In one embodiment, the correlation between the real-time ground truth data and the RX-converted data is executed to determine whether the RX-converted data corresponds to the real-time ground truth data. For example, the module may execute the correlation between the real-time ground truth data related to the blood glucose level of the patient as 110 mg/dL corresponding to the radio signal of frequency 122 GHZ, and the 8-bit data corresponding to Activated RF range 140-155 GHz. For example, the memory 110 may store the real-time ground truth data and RX converted data. For example, the memory 110 stores the real-time ground truth data related to the blood glucose level of the patient as 110 mg/dL corresponding to the radio signal of frequency 122 GHZ, and the 8-bit data corresponding to Activated RF range 140-155 GHZ.

Further, embodiments may include a lookup database 132 which is used in the process described in the integration module 122 to determine the modules the base module 120 will execute to detect the analyte inputted into the user interface 118. The database 132 contains the mode, such as one, two, three, etc. the first module executed, the second module executed, if needed, the third module executed, if needed, and the analyte the mode detects. The database 132 may be created using historical data stored in the enhancement database 130 which contains data entries that included the best sent transmission signal for the TX antenna 104, the length of the sent transmission signal, the expected received transmission signal from the RX antenna 106, the filter used by the RX antenna 106, and the analyte that may be detected. For example, there may be a sequence of transmission signals that are best to detect a certain analyte, such as glucose, sodium, potassium, etc. which would allow the sending enhancement module 126 and receiving enhancement module 128 to extract the specific sequence from the enhancement database 130 to detect the specific analyte. For example, the best mode may be to send all the transmission signals stored in the enhancement database 130 in which the transmission module 124 would be executed. In some embodiments, the transmission module 124, sending enhancement module 126, or receiving enhancement module 128 may be executed individually or in combination with one or two other modules.

FIG. 2 illustrates an example operation of the base module 120. The process begins with the base module 120 initiating, at step 200, the integration module 122. For example, the integration module 122 begins by being initiated by the base module 120. The integration module 122 receives the analyte from the user interface 118. The integration module 122 compares the received analyte from the user interface 118 to the lookup database 132. The integration module 122 extracts the mode from the lookup database 132. The integration module 122 sends the extracted mode to the base module 120. The integration module 122 then returns to the base module 120. The base module 120 is continuously polling, at step 202, for the mode from the integration module 122. For example, the base module 120 is continuously polling to receive the mode from the integration module 122 which provides the base module 120 with instructions on which modules to initiate. For example, there may be a sequence of transmission signals that are best to detect a certain analyte, such as glucose, sodium, potassium, etc. which would allow the sending enhancement module 126 and receiving enhancement module 128 to extract the specific sequence from the enhancement database 130 to detect the specific analyte. For example, the best mode may be to send all the transmission signals stored in the enhancement database 130 in which the transmission module 124 would be executed. In some embodiments, the transmission module 124, sending enhancement module 126, or receiving enhancement module 128 may be executed individually or in combination with one or two other modules. The base module 120 receives, at step 204, the mode from the integration module 122. For example, the base module 120 receives the mode from the integration module 122 which provides the base module 120 with instructions on which modules to initiate. For example, there may be a sequence of transmission signals that are best to detect a certain analyte, such as glucose, sodium, potassium, etc. which would allow the sending enhancement module 126 and receiving enhancement module 128 to extract the specific sequence from the enhancement database 130 to detect the specific analyte. For example, the best mode may be to send all the transmission signals stored in the enhancement database 130 in which the transmission module 124 would be executed. In some embodiments, the transmission module 124, sending enhancement module 126, or receiving enhancement module 128 may be executed individually or in combination with one or two other modules. The base module 120 determines, at step 206, if the transmission module 124 should be initiated. For example, the base module 120 may store the received mode from the integration module 122 in memory 110 and compare the data from the transmission module 124 to the mode in memory 110 to determine if the transmission module 124 should be initiated. If it is determined that the transmission module 124 should be initiated, the base module 120 initiates, at step 208, the transmission module 124. For example, the transmission module 124 begins by being initiated by the base module 120. The transmission module 124 extracts the first transmission signal from the enhancement database 130. The transmission module 124 sends the RF transmit signal to the TX antenna 104. The transmission module 124 activates the RX antennas 106, and receives the RF signal from the RX antenna 106. The transmission module 124 determines if there are more transmission signals remaining in the enhancement database 130. If it is determined that there are more transmission signals remaining in the enhancement database 130, the transmission module 124 extracts the next transmission signal from the enhancement database 130 and returns to sending the RF transmit signal to the TX antenna 104. If it is determined that there is no more transmission signals remaining in the enhancement database 130, the transmission signal returns to the base module 120. In some embodiments, the transmission module 124 may be initiated after the sending enhancement module 126 and receiving enhancement module 128. In some embodiments, the transmission module 124 may receive the transmit signals and RX antenna 106 settings from the sending enhancement module 126 and receiving enhancement module 128, respectively. If it is determined that the transmission module 124 should not be initiated or after the transmission module 124 is initiated, the base module 120 determines, at step 210, if the sending enhancement module 126 should be initiated. For example, the base module 120 may store the received mode from the integration module 122 in memory 110 and compare the data from the sending enhancement module 126 to the mode in memory 110 to determine if the sending enhancement module 126 should be initiated. If it is determined that the sending enhancement module 126 should be initiated, the base module 120 initiates, at step 212, the sending enhancement module 126. For example, the sending enhancement module 126 begins with the sending enhancement module 126 being initiated by the base module 120. The sending enhancement module 126 filters the enhancement database 130 on the correct transmission signals. The sending enhancement module 126 extracts the first correct transmit signal from the enhancement database 130. The sending enhancement module 126 sends the correct transmit signal to the TX antenna 104. The sending enhancement module 126 determines if there are more transmit signals remaining in the enhancement database 130. If it is determined that there are more transmit signals remaining in the enhancement database 130, the sending enhancement module 126 extracts the next transmit signal from the enhancement database 130 and returns to sending the transmit signal to the TX antenna 104. If it is determined that there are no more transmit signals remaining in the enhancement database 130, the sending enhancement module 126 returns to the base module 120. In some embodiments, the sending enhancement module 126 may be initiated prior to the transmission module 124. In some embodiments, the sending enhancement module 126 may filter and extract the data from the enhancement database 130 and then send the extracted data entries to the transmission module 124 to send the RX antenna 106 settings to the RX antenna 106 to prepare receiving the RF signal. If it is determined that the sending enhancement module 126 should not be initiated or after the sending enhancement module 126 is initiated, the base module 120 determines, at step 214, if the receiving enhancement module 128 should be initiated. If it is determined that the receiving enhancement module 128 should not be initiated, the base module 120 returns to initiating the integration module 122. For example, the base module 120 may store the received mode from the integration module 122 in memory 110 and compare the receiving enhancement module 128 to the mode in memory 110 to determine if the receiving enhancement module 128 should be initiated. If it is determined that the receiving enhancement module 128 should be initiated, the base module 120 initiates, at step 216, the receiving enhancement module 128. For example, the receiving enhancement module 128 begins by being initiated by the base module 120. The receiving enhancement module 128 filters the enhancement database 130 on the correct receive antenna 106 settings. The receiving enhancement module 128 extracts the first setting from the enhancement database 130. The receiving enhancement module 128 receives the RF signal from the RX antenna 106 with the extracted settings from the enhancement database 130. The receiving enhancement module 128 determines if there are more settings remaining in the enhancement database 130. If it is determined that there are more settings remaining in the enhancement database 130, the receiving enhancement module 128 extracts the next setting in the enhancement database 130 and returns to receiving the RF signal from the RX antenna 106. If it is determined that there are no more settings remaining in the enhancement database 130, the receiving enhancement module 128 returns to the base module 120. In some embodiments, the receiving enhancement module 128 may be initiated prior to the transmission module 124. In some embodiments, the receiving enhancement module 128 may filter and extract the data from the enhancement database 130 and then send the extracted data entries to the transmission module 124 to send the RX antenna 106 settings to the RX antenna 106 to prepare receiving the RF signal.

FIG. 3 illustrates an example operation of the integration module 122. The process begins with the integration module 122 being initiated, at step 300, by the base module 120. The integration module 122 receives, at step 302, the analyte from the user interface 118. For example, the user may input the desired analyte to be detected in the user interface 118 and the analyte may be sent to the integration module 122. In some embodiments, the integration module 122 may be continuously polling to receive the analyte from the user interface 118 and be initiated once the analyte is inputted. The integration module 122 compares, at step 304, the received analyte from the user interface 118 to the lookup database 132. For example, the integration module 122 compares the received analyte from the user interface 118 to the list of analytes stored in the lookup database 132, such as glucose, sodium, potassium, chloride, etc. The integration module 122 extracts, at step 306, the mode from the lookup database 132. For example, the integration module 122 extracts the mode from the lookup database that corresponds to the analyte received from the user interface 118. For example, mode may be used to determine the modules the base module 120 will execute to detect the analyte inputted into the user interface 118. The database 132 contains the mode, such as one, two, three, etc. the first module executed, the second module executed, if needed, the third module executed, if needed, and the analyte the mode detects. The database 132 may be created using historical data stored in the enhancement database 130 which contains data entries that included the best sent transmission signal for the TX antenna 104, the length of the sent transmission signal, the expected received transmission signal from the RX antenna 106, the filter used by the RX antenna 106, and the analyte that may be detected. The integration module 122 sends, at step 308, the extracted mode to the base module 120. For example, the integration module 122 sends the mode which includes the modules to executed to the base module 120. For example, there may be a sequence of transmission signals that are best to detect a certain analyte, such as glucose, sodium, potassium, etc. which would allow the sending enhancement module 126 and receiving enhancement module 128 to extract the specific sequence from the enhancement database 130 to detect the specific analyte. For example, the best mode may be to send all the transmission signals stored in the enhancement database 130 in which the transmission module 124 would be executed. In some embodiments, the transmission module 124, sending enhancement module 126, or receiving enhancement module 128 may be executed individually or in combination with one or two other modules. The integration module 122 then returns, at step 310, to the base module 120.

FIG. 4 illustrates an example operation of the transmission module 124. The process begins with the transmission module 124 being initiated, at step 400, by the base module 120. For example, the base module 120 may initiate the transmission module 124 if the mode received by the base module 120 from the integration module 122 included executing the transmission module 124. In some embodiments, the integration module 122 may extract the mode from the lookup database 132 and initiate the transmission module 124 if included in the extracted mode. The transmission module 124 extracts, at step 402, the first transmission signal from the enhancement database 130. For example, the transmission module may extract the first transmission signal that is sent to the TX antenna 104 from the enhancement database 130. For example, the enhancement database 130 contains a plurality of transmission signal procedures which may include the transmission signal ID, the RF transmit signal, the duration the signal is transmitted, the expected received signal, the filter settings, and the analyte that may be detected during the procedure. The database may be created using historical information collected in a clinical setting in which the transmit and received signals, as well as the duration and filter settings, are monitored to determine if an analyte is detected. The transmission module 124 sends, at step 404, the RF transmit signal to the TX antenna 104. For example, the one or more TX antennas 104 may be configured to transmit the Activated RF range signals at a pre-defined frequency. In one embodiment, the pre-defined frequency may correspond to a range suitable for the human body. For example, the one or more TX antennas 104 transmit Activated RF range signals at a range of 122-126 GHz. The transmission module 124 activates, at step 406, the RX antennas 106. For example, the transmission module 124 may activate the RX antennas 106 to receive the resulting signal. The transmission module 124 may also extract the filter settings stored in the enhancement database 130 to adjust the settings of the RX antenna 106 to receive the expected signal. The transmission module 124 receives, at step 408, the RF signal from the RX antenna 106. For example, the one or more RX antennas 106 may be configured to receive the responded portion of the Activated RF range signals. The transmission module 124 determines, at step 410, if there are more transmission signals remaining in the enhancement database 130. For example, the transmission module 124 determines if all of the transmit signals have been extracted from the enhancement database 130 and sent to the TX antennas 104. The transmission module 124 may extract and send each of the plurality of transmit signals stored in the enhancement database 130 individually. If it is determined that there are more transmission signals remaining in the enhancement database 130, the transmission module 124 extracts, at step 412, the next transmission signal from the enhancement database 130 and returns to sending the RF transmit signal to the TX antenna 104. For example, once the transmit signal is received by the RX antenna 106 and it is determined that there are more transmit signals remaining in the enhancement database 130, the transmission module 124 extracts the next transmit signal in the enhancement database 130 and sends the transmit signal to the TX antenna 104 to be transmitted. If it is determined that there are no more transmission signals remaining in the enhancement database 130, the transmission signal returns, at step 414, to the base module 120. For example, once all of the transmit signals stored in the enhancement database 130 have been extracted and sent by the TX antennas 104 and the signals have been received by the RX antenna 106, the transmission module 124 returns to the base module 120.

FIG. 5 illustrates an example operation of the sending enhancement module 126. The process begins with the sending enhancement module 126 being initiated, at step 500, by the base module 120. For example, the base module 120 may initiate the sending enhancement module 126 if the mode received by the base module 120 from the integration module 122 included executing the sending enhancement module 126. In some embodiments, the integration module 122 may extract the mode from the lookup database 132 and initiate the sending enhancement module 126 if included in the extracted mode. The sending enhancement module 126 filters, at step 502, the enhancement database 130 on the correct transmission signals. For example, the sending enhancement module 126 may filter the enhancement database 130 on the correct transmission signals by filtering the enhancement database 130 on the analyte that was inputted in the user interface 118 and received by the integration module 122. In some embodiments, the integration module 122 may send the inputted analyte to the sending enhancement module 126. In some embodiments, the integration module 122 may send the analyte inputted by the user interface 118 to the base module 120 and the base module 120 may send the inputted analyte to the sending enhancement module 126. The sending enhancement module 126 extracts, at step 504, the first correct transmit signal from the enhancement database 130. For example, the sending enhancement module 126 extracts the first correct transmit signal from the filtered enhancement database 130. For example, if the inputted analyte was glucose, the sending enhancement module 126 would filter the enhancement database 130 on the data entries that include glucose as the desired analyte and then extract the first transmit signal from the first data entry. Then the sending enhancement module 126 would send the extracted transmit signal to the TX antenna 104 to transmit the extracted signal. The sending enhancement module 126 sends, at step 506, the correct transmit signal to the TX antenna 104. For example, the sending enhancement module 126 would filter the enhancement database 130 on the data entries that include glucose as the desired analyte and then extract the first transmit signal from the first data entry. Then the sending enhancement module 126 would send the extracted transmit signal to the TX antenna 104 to transmit the extracted signal. In some embodiments, the sending enhancement module 126 may filter and extract the data from the enhancement database 130 and then send the extracted data entries to the transmission module 124 to send the transmit signals to the TX antennas 104. In some embodiments, the sending enhancement module 126 may send a signal to the receiving enhancement module 128 that a transmit signal has been sent and be continuously polling until the receiving enhancement module 128 has received the signal from the RX antennas 106 to ensure that the sending enhancement module 126 is waiting the appropriate amount of time to send the next transmit signal without interfering with the previously sent transmit signal. The sending enhancement module 126 determines, at step 508, if there are more transmit signals remaining in the enhancement database 130. For example, the sending enhancement module 126 determines if all of the transmit signals have been extracted from the filtered enhancement database 130 and sent to the TX antennas 104. The sending enhancement module 126 may extract and send each of the plurality of transmit signals stored in the filtered enhancement database 130 individually. If it is determined that there are more transmit signals remaining in the enhancement database 130, the sending enhancement module 126 extracts, at step 510, the next transmit signal from the enhancement database 130 and returns to sending the transmit signal to the TX antenna 104. For example, once the transmit signal is received by the RX antenna 106 and it is determined that there is more transmit signals remaining in the filtered enhancement database 130, the sending enhancement module 126 extracts the next transmit signal in the filtered enhancement database 130 and sends the transmit signal to the TX antenna 104 to be transmitted. In some embodiments, the sending enhancement module 126 may send a signal to the receiving enhancement module 128 that a transmit signal has been sent and be continuously polling until the receiving enhancement module 128 has received the signal from the RX antennas 106 to ensure that the sending enhancement module 126 is waiting the appropriate amount of time to send the next transmit signal without interfering with the previously sent transmit signal. If it is determined that there are no more transmit signals remaining in the enhancement database 130, the sending enhancement module 126 returns, at step 512, to the base module 120.

FIG. 6 illustrates an example operation of the receiving enhancement module 128. The process begins with the receiving enhancement module 128 being initiated, at step 600, by the base module 120. For example, the base module 120 may initiate the receiving enhancement module 128 if the mode received by the base module 120 from the integration module 122 included executing the receiving enhancement module 128. In some embodiments, the integration module 122 may extract the mode from the lookup database 132 and initiate the receiving enhancement module 128 if included in the extracted mode. The receiving enhancement module 128 filters, at step 602, the enhancement database 130 on the correct receive antenna 106 settings. For example, the receiving enhancement module 128 may filter the enhancement database 130 on the correct response signals expected and RX antenna settings by filtering the enhancement database 130 on the analyte that was inputted in the user interface 118 and received by the integration module 122. In some embodiments, the integration module 122 may send the inputted analyte to the receiving enhancement module 128. In some embodiments, the integration module 122 may send the analyte inputted by in the user interface 118 to the base module 120 and the base module 120 may send the inputted analyte to the receiving enhancement module 128. The receiving enhancement module 128 extracts, at step 604, the first setting from the enhancement database 130. For example, the receiving enhancement module 126 extracts the first correct RX antenna 106 setting from the filtered enhancement database 130. For example, if the inputted analyte was glucose, the receiving enhancement module 128 would filter the enhancement database 130 on the data entries that include glucose as the desired analyte and then extract the first RX antenna 106 setting from the first data entry. Then the receiving enhancement module 128 would send the extracted RX antenna 106 settings to the RX antenna 106 to receive the signal. For example, the RX antenna 106 settings may include settings for low pass filters, band pass filters, mixer settings, etc. For example, a low pass filter is a filter that passes signals with a frequency lower than a selected cutoff frequency and attenuates signals with frequencies higher than the cutoff frequency. The exact frequency response of the filter depends on the filter design. For example, a band pass filter is a device that passes frequencies within a certain range and rejects frequencies outside that range. The RX antenna 106 settings may be implemented to receive an expected signal from the RX antenna 106. In some embodiments, once the RF signal is received by the RX antenna 106, the receiving enhancement module 128 may compare the received RF signal to the enhancement database 130 to ensure that the correct signals are being received from the RX antenna 106. The receiving enhancement module 128 receives, at step 606, the RF signal from the RX antenna 106 with the extracted settings from the enhancement database 130. For example, the receiving enhancement module 128 receives the RF signal from the RX antenna 106. For example, the receiving enhancement module 128 may receive a signal from the sending enhancement module 126 that a transmit signal is being sent and the receiving enhancement module 128 may be continuously polling to receive the signal from the sending enhancement module 126 once the RX antenna 106 settings have been extracted and sent to the RX antenna 106 to prepare receiving the RF signal from the RX antennas 106. In some embodiments, the receiving enhancement module 128 may filter and extract the data from the enhancement database 130 and then send the extracted data entries to the transmission module 124 to send the RX antenna 106 settings to the RX antenna 106 to prepare receiving the RF signal. The receiving enhancement module 128 determines, at step 608, if there are more settings remaining in the enhancement database 130. For example, the receiving enhancement module 128 determines if all of the RX antenna 106 settings have been extracted from the filtered enhancement database 130 and sent to the RX antennas 106. The receiving enhancement module 128 may extract and send each of the plurality of RX antenna 106 settings stored in the filtered enhancement database 130 individually. If it is determined that there are more settings remaining in the enhancement database 130, the receiving enhancement module 128 extracts, at step 610, the next setting in the enhancement database 130 and returns to receiving the RF signal from the RX antenna 106. For example, once the RF signal is received by the RX antenna 106 and it is determined that there is more transmit signals remaining in the filtered enhancement database 130, the receiving enhancement module 128 extracts the next RX antenna 106 settings in the filtered enhancement database 130 and sends the settings to the RX antenna 106 to receive the next RF signal. In some embodiments, the receiving enhancement module 128 may receive a signal from the sending enhancement module 126 that a transmit signal has been sent and be continuously polling until the RF signal has been received from the signal from the RX antennas 106 and sends a signal to the sending enhancement module 126 that the RF signal has been received. If it is determined that there are no more settings remaining in the enhancement database 130, the receiving enhancement module 128 returns, at step 612, to the base module 120.

FIG. 7 illustrates an example of the enhancement database 130. The database 130 may contain a plurality of transmission signal procedures which may include the transmission signal ID, the RF transmit signal, the duration the signal is transmitted, the expected received signal, the filter settings, and the analyte that may be detected during the procedure. The database 130 may be created using historical information collected in a clinical setting in which the transmit and received signals, as well as the duration and filter settings, are monitored to determine if an analyte is detected. The detection of the analyte may be based upon comparing the transmit signals and received signals to ground truth data collected by medical devices. For example, the database 130 may utilize a module that may be configured to execute an AI correlation between the real-time ground truth data and the RX converted data. In one embodiment, the AI correlation between the real-time ground truth data and the RX-converted data is executed to determine whether the RX-converted data corresponds to the real-time ground truth data. For example, the module may execute the AI correlation between the real-time ground truth data related to the blood glucose level of the patient as 110 mg/dL corresponding to the radio signal of frequency 122 GHZ, and the 8-bit data corresponding to Activated RF range 140-155 GHz. For example, the memory 104 may store the real-time ground truth data and RX converted data. For example, the memory 104 stores the real-time ground truth data related to the blood glucose level of the patient as 110 mg/dL corresponding to the radio signal of frequency 122 GHZ, and the 8-bit data corresponding to Activated RF range 140-155 GHZ.

FIG. 8 illustrates an example of the lookup database 132. The database 132 is used in the process described in the integration module 122 to determine the modules the base module 120 will execute to detect the analyte inputted into the user interface 118. The database 132 contains the mode, such as one, two, three, etc. the first module executed, the second module executed, if needed, the third module executed, if needed, and the analyte the mode detects. The database 132 may be created using historical data stored in the enhancement database 130 which contains data entries that included the best sent transmission signal for the TX antenna 104, the length of the sent transmission signal, the expected received transmission signal from the RX antenna 106, the filter used by the RX antenna 106, and the analyte that may be detected. For example, there may be a sequence of transmission signals that are best to detect a certain analyte, such as glucose, sodium, potassium, etc. which would allow the sending enhancement module 126 and receiving enhancement module 128 to extract the specific sequence from the enhancement database 130 to detect the specific analyte. For example, the best mode may be to send all the transmission signals stored in the enhancement database 130 in which the transmission module 124 would be executed. In some embodiments, the transmission module 124, sending enhancement module 126, or receiving enhancement module 128 may be executed individually or in combination with one or two other modules.

The functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The invention claimed is:

1. A non-invasive analyte detection system, comprising:

a non-invasive radio-frequency (RF) analyte detection device that includes one or more transmit antennas configured to transmit RF analyte detection signals from the one or more transmit antennas into a user, and one or more receive antennas that receive return RF analyte signals that result from the RF analyte detection signals transmitted into the user; the non-invasive RF analyte detection device is configured to perform an analyte detection routine using the one or more transmit antennas and the one or more receive antennas;

an analog-to-digital converter connected to the one or more receive antennas;

a user interface of the non-invasive RF analyte detection device, the user interface is configured to allow user input of an analyte to be detected during the analyte detection routine;

a look-up database that includes a plurality of stored modes; each stored mode includes at least one executable module to be executed and a corresponding analyte, and the stored modes are different from one another;

an enhancement database that includes a plurality of stored transmission signal procedures, each stored transmission signal procedure includes an RF transmit signal to be transmitted, an expected RF received signal corresponding to the RF transmit signal, and an associated analyte, and the stored transmission signal procedures are different from one another.

2. The non-invasive analyte detection system of claim 1, further comprising:

an integration module in communication with the user interface and with the look-up database that is configured to selected one of the stored modes based on the analyte to be detected input via the user interface and configured to extract the at least one executable module to be executed corresponding to the selected stored mode.

3. The non-invasive analyte detection system of claim 1, wherein the at least one executable module of each stored mode comprises at least one of a transmission module, a sending enhancement module, and a receiving enhancement module; and the at least one executable module is in communication with the enhancement database.

4. The non-invasive analyte detection system of claim 1, wherein each stored mode of the look-up database includes a plurality of executable modules to be executed.

5. The non-invasive analyte detection system of claim 4, wherein the plurality of executable modules of each stored mode comprises two or more of a transmission module, a sending enhancement module, and a receiving enhancement module; and each one of the executable modules is in communication with the enhancement database.

6. The non-invasive analyte detection system of claim 1, further comprising an executable module in communication with the enhancement database, the executable module is configured to select and utilize data from one or more of the stored transmission signal procedures.

7. The non-invasive analyte detection system of claim 1, wherein each stored transmission signal procedure further includes a transmit signal length and a filter setting.

8. A non-invasive analyte detection system, comprising:

a non-invasive radio-frequency (RF) analyte detection device that includes one or more transmit antennas configured to transmit RF analyte detection signals from the one or more transmit antennas into a user, and one or more receive antennas that receive return RF analyte signals that result from the RF analyte detection signals transmitted into the user; the non-invasive RF analyte detection device is configured to perform an analyte detection routine using the one or more transmit antennas and the one or more receive antennas;

an analog-to-digital converter connected to the one or more receive antennas;

a look-up database that includes a plurality of stored modes; each stored mode includes at least one executable module to be executed and a corresponding analyte, and the stored modes are different from one another;

an enhancement database that includes a plurality of stored transmission signal procedures, each stored transmission signal procedure includes an RF transmit signal to be transmitted, an expected RF received signal corresponding to the RF transmit signal, and an associated analyte, and the stored transmission signal procedures are different from one another.

9. The non-invasive analyte detection system of claim 8, further comprising:

an integration module in communication with the look-up database that is configured to selected one of the stored modes based on an analyte to be detected and configured to extract the at least one executable module to be executed corresponding to the selected stored mode.

10. The non-invasive analyte detection system of claim 8, wherein the at least one executable module of each stored mode comprises at least one of a transmission module, a sending enhancement module, and a receiving enhancement module; and the at least one executable module is in communication with the enhancement database.

11. The non-invasive analyte detection system of claim 8, wherein each stored mode of the look-up database includes a plurality of executable modules to be executed.

12. The non-invasive analyte detection system of claim 11, wherein the plurality of executable modules of each stored mode comprises two or more of a transmission module, a sending enhancement module, and a receiving enhancement module; and each one of the executable modules is in communication with the enhancement database.

13. The non-invasive analyte detection system of claim 8, further comprising an executable module in communication with the enhancement database, the executable module is configured to select and utilize data from one or more of the stored transmission signal procedures.

14. The non-invasive analyte detection system of claim 8, wherein each stored transmission signal procedure further includes a transmit signal length and a filter setting.

15. A non-invasive analyte detection method, comprising:

providing a non-invasive radio-frequency (RF) analyte detection device that includes one or more transmit antennas configured to transmit RF analyte detection signals from the one or more transmit antennas into a user, and one or more receive antennas that receive return RF analyte signals that result from the RF analyte detection signals transmitted into the user; the non-invasive RF analyte detection device is configured to perform an analyte detection routine using the one or more transmit antennas and the one or more receive antennas;

receiving a selection of a desired analyte to be detected by the non-invasive RF analyte detection device;

based on the desired analyte, accessing a look-up database and comparing the desired analyte to a plurality of stored modes each of which includes at least one corresponding executable module to be executed and a corresponding analyte;

if one of the stored modes has a corresponding analyte that corresponds to the desired analyte, selecting the one stored mode and extracting the at least one corresponding executable module of the one stored mode;

thereafter the extracted at least one corresponding executable module accessing an enhancement database that includes a plurality of stored transmission signal procedures each of which includes an RF transmit signal to be transmitted, an expected RF received signal corresponding to the RF transmit signal, and an associated analyte; and the extracted at least one corresponding executable module executing one or more of the stored transmission signal procedures having an associated analyte that corresponds to the desired analyte.

16. The non-invasive analyte detection method of claim 15, wherein the desired analyte is input by a user via an integration module that is in communication with the look-up database.

17. The non-invasive analyte detection method of claim 15, wherein the at least one corresponding executable module of each stored mode comprises at least one of a transmission module, a sending enhancement module, and a receiving enhancement module.

18. The non-invasive analyte detection method of claim 15, wherein each stored mode of the look-up database includes a plurality of executable modules to be executed; and if one of the stored modes has a corresponding analyte that corresponds to the desired analyte, selecting the one stored mode and extracting a plurality of executable modules to be executed.

19. The non-invasive analyte detection method of claim 15, comprising filtering the enhancement database to generate a filtered subset of the stored transmission signal procedures, and executing the filtered subset of the stored transmission signal procedures.

* * * * *